(12) United States Patent
Pawlowski et al.

(10) Patent No.: US 6,336,357 B1
(45) Date of Patent: Jan. 8, 2002

(54) METHOD AND APPARATUS FOR SEALING TEST MATERIALS

(76) Inventors: Henry Pawlowski, 3671 Good Rd., Seville, OH (US) 44273; Xiaofeng Xu, 2220 High St., Apt. 804, Cuyahoga Falls, OH (US) 44221

( * ) Notice: Subject to any disclaimer, the term of this patent is extended or adjusted under 35 U.S.C. 154(b) by 0 days.

(21) Appl. No.: 09/270,266

(22) Filed: Mar. 15, 1999

(51) Int. Cl.$^7$ ............................................. G01N 11/00
(52) U.S. Cl. ...................................................... 73/54.33
(58) Field of Search ........................... 73/54.28, 54.29, 73/54.31–54.34, 54.39, 841, 843, 54.33

(56) References Cited

U.S. PATENT DOCUMENTS

| | | |
|---|---|---|
| 4,497,201 A | 2/1985 | Allen et al. |
| 4,601,195 A * | 7/1986 | Garritano ................... 73/54.34 |
| 4,953,406 A | 9/1990 | Putman |
| 5,079,956 A | 1/1992 | Burhin et al. |
| 5,551,535 A | 9/1996 | Krolo et al. ................ 188/72.2 |
| 5,806,833 A | 9/1998 | Riibe ................................... |

* cited by examiner

*Primary Examiner*—Robert Raevis

(57) ABSTRACT

An improved method and apparatus for measuring the properties of thermoset plastics and viscoelastic materials. The present invention includes a seal member which inhibits the release of sample material from the die cavity of a test instrument. As a result, sufficient sample material is maintained within the die cavity when pressure is applied to the material. Accordingly, an appropriate shearing force can be applied to the sample material to obtain torque measurements. Moreover, by inhibiting the release of sample material from the die cavity, sample material is prevented from coming into contact with components of the test instrument outside the die cavity, which in turn may distort or invalidate measurements of torque.

21 Claims, 3 Drawing Sheets

METHOD AND APPARATUS FOR SEALING TEST MATERIALS

FIELD OF INVENTION

The present invention generally relates to an improved method and apparatus for measuring the properties of thermoset plastics and viscoelastic materials, and more specifically to method and apparatus for sealing thermoset plastics and viscoelastic materials during testing thereof.

BACKGROUND OF THE INVENTION

In the prior art, there are many well known instruments for determining various properties of viscoelastic materials (e.g., rubber and like materials). These instruments include such apparatus commonly referred to as Moving Die Rheometers (MDR), Rubber Process Analyzers (RPA), Oscillating Disk Rheometers (ODR), and Mooney Viscometers. These instruments apply a rotational shear strain to a sample material and measure the resulting torque. It should be understood that the applied rotational shear may be oscillatory or continuous. In the case of an MDR or RPA, a sample material to be tested is enclosed in a cavity formed between two opposing die plates, and the rotational shear is applied to the sample by rotating one die plate, while the other die plate remains stationary, and the torque required to apply the shear is measured. In the case of an ODR or Mooney Viscometer sample material to be tested is enclosed in a cavity formed between two opposing die plates, rotational shear is applied to the sample material by means of a rotor embedded in the sample, and the torque required to apply the shear is measured. In U.S. Pat. Nos. 3,479,858; 4,343,190; and 4,552,025, the force is applied by rotation of one die plate relative to the other, and the measurements made are of the torque required to apply the shearing force or of the torque induced in the second die plate (reaction torque) when the first (driven) die plate is rotated. It should be noted that testing of sample materials is typically a period of 1 minute to 24 hours.

An exemplary prior art instrument is shown in FIG. 1. It should be appreciated that a variety of other similar instruments, such as those noted above, are also suitable for use in connection with the present invention. Apparatus A1 includes members 1, 2 and 3, which are respectively left and right vertical and horizontal components of an outer frame which is supported on a base (not shown). A lower die assembly comprising a lower die housing 4 and a housing 5 for a drive shaft 6, is mounted in the horizontal member 3. Drive shaft 6 is connected at its upper end to a lower die plate (not shown). An inner frame, which is located beneath horizontal member 3 has vertical portions 7 and 8, and a lower horizontal portion 9. Tie rods 10 and 11, which pass through horizontal member 3, are attached at their lower ends to a lower crosshead 13. An upper die assembly, comprising an upper die housing 14, is mounted in an upper crosshead 12. A pneumatic cylinder 15 mounted beneath the horizontal portion 9 of the inner frame has a cylinder rod 16 which is connected to the lower crosshead 13. Actuation of pneumatic cylinder 15 causes the assembly consisting of a cylinder rod 16, lower crosshead 13, tie rods 10, 11 and upper crosshead 12 to travel downwards, thus bringing upper die housing 14, lower die housing 4, and the die plates into the closed position. The drive system to the lower die plate includes a computer controlled electric motor 17, mounted with its output shaft 18 coaxial with drive shaft 6 to the lower die plate. The two shafts 18, 6 are coupled by means of a sleeve 19.

General operation of a typical instrument for measuring the properties of viscoelastic materials is as follows: The two opposing die plates are first moved to an open position, so that a sample of viscoelastic material can be placed between the die plates. In some cases the sample will be sandwiched between layers of film. Next, the two opposing die plates are moved to a closed position to form a test cavity, wherein the sample of viscoelastic material is maintained under pressure. The temperature of the die plates is controlled during the measurement process. The sample is then subjected to an oscillating, rotary shear force having a predetermined amplitude and frequency. A torque is measured, which is indicative of the response of the sample to the shearing force. Information is derived on the properties of the material from such measurements. It should be appreciated that the shear force is applied to the sample by rotation of one die plate relative to the other. The torque measurements are the torque required to apply the shearing force or of the torque induced in the second die plate (reaction torque) when the first die plate (driven) is rotated. It should be appreciated that other suitable arrangements are also possible.

While the instruments described above are suitable for testing relatively high viscosity rubbery viscoelastic materials, several problems are encountered when such instruments are used to test relatively low viscosity materials, such as thermoset plastics (e.g., resins). One of these problems relates to containment of the low viscosity sample material within the die cavity. If too much sample material flows out of the die cavity when pressure is applied to the sample material in the die cavity, an appropriate torque measurement cannot be made. In this regard, if there is an insufficient gripping of the sample material as the shearing force is applied, the torque measurements will be invalid.

Another problem relates to bonding of low viscosity sample materials to components of the test instrument outside the die cavity. In this respect, low viscosity materials such as thermoset plastics are good adhesives, and when they set up they harden and bond to surfaces. This may occur during a curing procedure. Adherence to components such as sealing plates, will distort torque measurements. This problem is referred to as "grounding."

Accordingly, there is a need for a method and apparatus that will contain a low viscosity test material within a die cavity and prevent grounding.

SUMMARY OF THE INVENTION

According to the present invention there is provided a containment system comprising: (a) a first die assembly including a first die plate having a first diameter; (b) a second die assembly including a second die plate rotatable relative to said first die plate and having the first diameter, wherein said first and second die assemblies are movable between an open and closed position, said first and second die plates forming a die cavity for holding a sample material; and (c) a sealing means located between said first and second die plates to inhibit release of the sample material from the die cavity.

According to another aspect of the present invention there is provided a method for inhibiting the release of a sample material from a die cavity of a test instrument for measuring properties of the sample material, wherein said die cavity is defined by first and second die plates which are movable between an open and closed position, said method comprising: moving the first and second die plates to the open position; locating a generally annular seal means between said first and second die plates; locating the sample material within an opening bounded by said seal means; and moving said first and second die plates to a closed position, wherein said seal means is compressed therebetween by the peripheral edges of said first and second die plates or sealing plates.

An advantage of the present invention is the provision of a containment system for inhibiting the release of low viscosity test material from a die cavity during testing thereof.

Another advantage of the present invention is the provision of a containment system for inhibiting the release of low viscosity test material from a die cavity when the test material is pressurized.

Still another advantage of the present invention is the provision of containment system for inhibiting the release of low viscosity test material from a die cavity when the test material is in a melt phase.

Yet another advantage of the present invention is the provision of containment system for inhibiting low viscosity test material in a die cavity from contacting mechanical components of the test instrument outside the die cavity.

Yet another advantage of the present invention is the provision of containment system for inhibiting the release of low viscosity test material a die cavity, and adhering to mechanical components of the test instrument outside the die cavity when the test material is in a cure phase.

Still other advantages of the invention will become apparent to those skilled in the art upon a reading and understanding of the following detailed description, accompanying drawings and appended claims.

BRIEF DESCRIPTION OF THE DRAWINGS

The invention may take physical form in certain parts and arrangements of parts, a preferred embodiment and method of which will be described in detail in this specification and illustrated in the accompanying drawings which form a part hereof, and wherein.

DETAILED DESCRIPTION OF THE PREFERRED EMBODIMENTS

Figure 1:
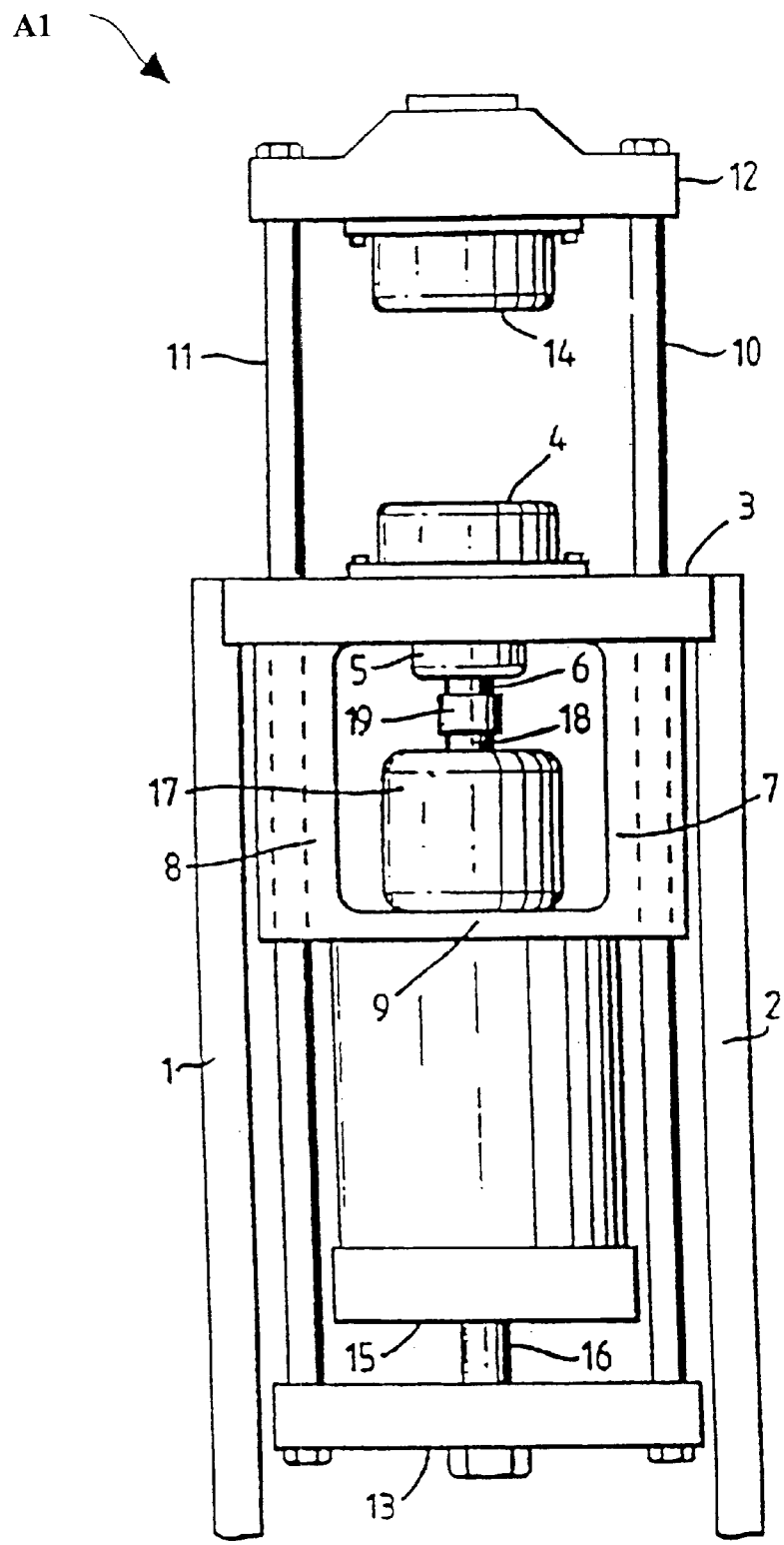
FIG. 1 is a front plan view of an exemplary prior art instrument for measuring the properties of viscoelastic materials.
Figure 2:
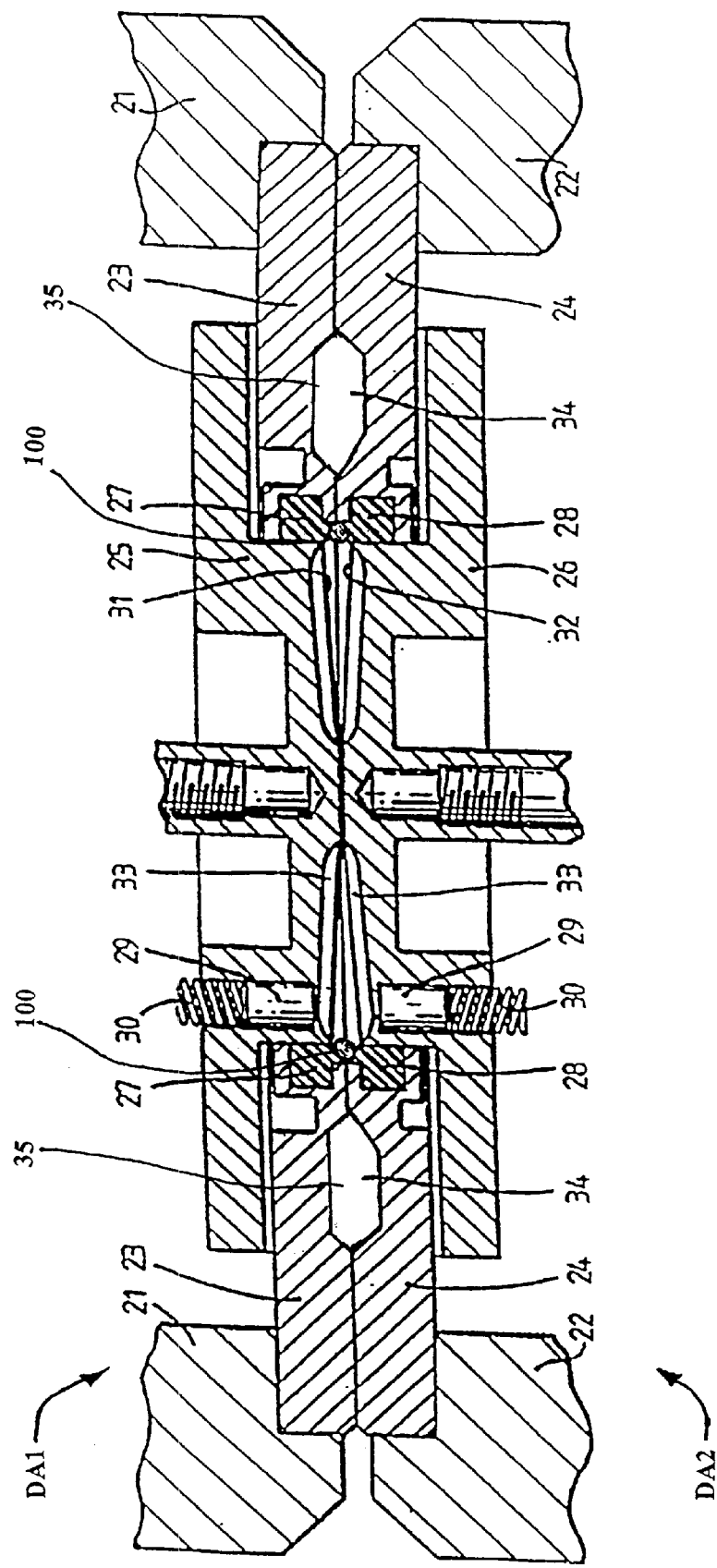
FIG. 2 is a vertical cross-section showing prior art die assemblies in the closed position.

Referring now to the drawings wherein the showings are for the purposes of illustrating a preferred embodiment of the invention only and not for purposes of limiting same, FIG. 2 illustrates the parts of typical upper and lower die assemblies DA1, DA2. The lower edge of the upper die housing and the upper edge of the lower die housing are indicated at 21 and 22 respectively. Other parts shown are upper and lower sealing plates 23 and 24, which are attached to the edges of the die housings, upper and lower die plates 25 and 26 respectively, and sealing rings 27 and 28. Each die plate 25, 26 has a cylindrical cavity 29 adapted to accommodate a temperature probe 30. The opposing faces 31 and 32 of die plates 25, 26, which define a die cavity, are in the form of shallow flat-topped cones (i.e., biconical plates) having radial grooves 33. Thus, a sample in the die cavity has a thin, flat circular portion the middle, and an outer portion which increases in thickness radially outwards. It should be appreciated that opposing faces 31 and 32 may have other configurations, including a generally planar surface (i.e., parallel plates). The biconical plate configuration is typically used for rubber materials, while the flat plate configuration is typically used for either rubber, plastic materials or resin impregnated fiber. The function of channels 34, 35 in lower and upper sealing plates 24, 23 is to accommodate any overflow of the sample material which is expressed during closure of the dies.

Parts of the upper and lower die assemblies DA1, DA2 which are not illustrated, being generally similar to those shown in FIG. 2 of U.S. Pat. No. 4,552,025 are (in upper die assembly DA1) a torque transducer, means connecting the upper die plate 25 to the force transducer, and heating elements; and in the lower die assembly DA2, a shaft coaxial with the lower die plate 26, means connecting the lower die plate 26 to the shaft, a bearing housing for the shaft, and heating elements for lower die plate 26.

As indicated above, the present invention provides means for containing sample material within the die cavity defined by upper and lower die plates 25, 26, during testing of the sample material. In accordance with a first embodiment of the present invention, this means takes the form of a deformable sealing member 100 (FIGS. 2 and 3), which inhibits the release of sample material from the die cavity. In a preferred embodiment, sealing member 100 has a generally annular or ring-like shape, with a generally circular cross-section. However, it should be understood that sealing member 100 may take other shapes, and have a cross-section of an alternative configuration, such as a generally triangular cross-section. Sealing member 100 is preferably formed of an elastomer, such as 75 durometer fluoroclastomer. An opening 102 defines an inner diameter ID1. Inner diameter ID1 of scaling member 100 is equal to or less than the diameter of upper and lower die plates 25, 26. Outer diameter OD1 is dimensioned such that the generally circular cross-section of sealing member 100 has a diameter that is greater than or equal to the distance between upper and lower die plates 25, 26 at the outer edge thereof.

Use of sealing member 100 will now be described in detail. First, the die plates 25 and 26 are moved to an open position. Sealing member 100 is then placed onto lower die plate 25, such that it is generally centered thereon, as shown in FIG. 2. An appropriate volume of sample material is then placed onto lower die plate 25 in the opening 102 defined by inner diameter ID1. Die plates 25,26 are then moved to a closed position, wherein a pressure is applied to both the sample material and sealing member 100. As a result, sealing member 100 will be compressed to some extent. Compression of sealing member 100 will cause it to deform and fill the gap between upper and lower die plates 25, 26, at the peripheral edges thereof. Moreover, compression of sealing member 100 may also cause it to fill a gap between upper and lower sealing rings 27 and 28 adjacent to die plates 25, 26. FIG. 2 illustrates sealing member 100 under compression. It should be appreciated that sealing member 100 is positioned such that it has minimal contact with the die plates 25, 26, but provides a barrier at the peripheral edge thereof. As a result, sealing member 100 itself does not have any significant effect on torque measurements.

In accordance with a second embodiment of the present invention, the means for containing sample material within the die cavity takes the form of a sealing member 110 having a generally disk-like shape. Sealing member 110 has generally planar upper and lower surfaces 114, 116. An opening 112 defines an inner diameter ID2, which is significantly less than outer diameter OD2 and the diameter of die plates 25, 26. Sealing member 110 is also preferably formed of an elastomer, such as 75 durometer fluoroelastomer. Moreover, outer diameter OD2 of sealing member 100 is equal to or less than the inner top diameter of upper and lower die plates 25, 26.

Sealing member 110 is used in generally the same manner as sealing member 100. However, there will be significant contact between sealing member 110 and die plates 25, 26. As a result, scaling member 110 itself will have an effect on torque measurements. Therefore, there will be a need to rin torque measurements with and without the presence of sample material in the die cavity. The net resulting difference in test results will provide accurate test results (i.e., torque values) for the sample material.

Figure 3:
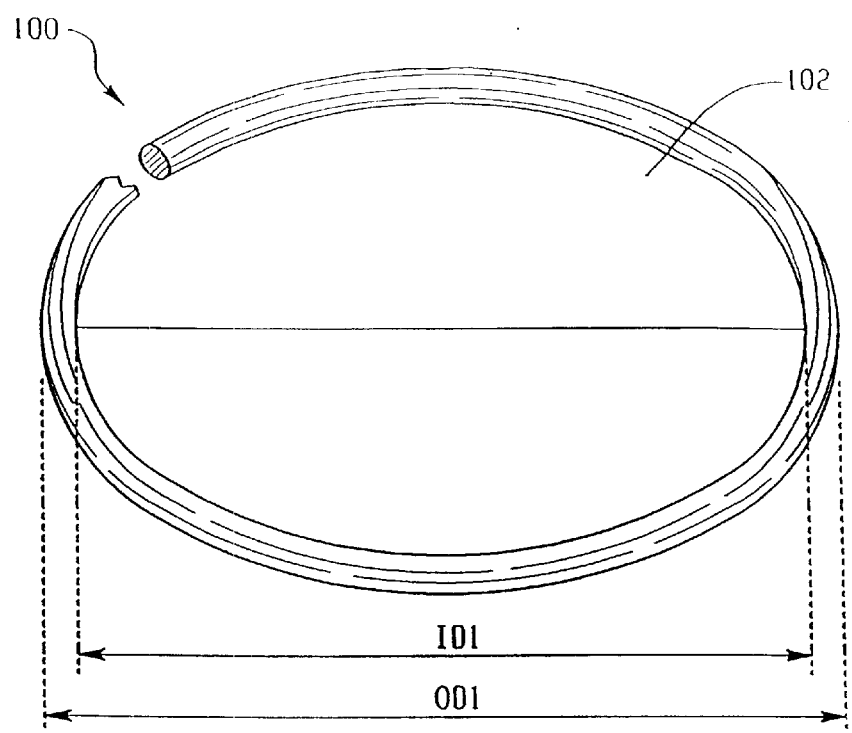
FIG. 3 is a perspective view of a seal member according to a first embodiment of the present invention.
Figure 4:
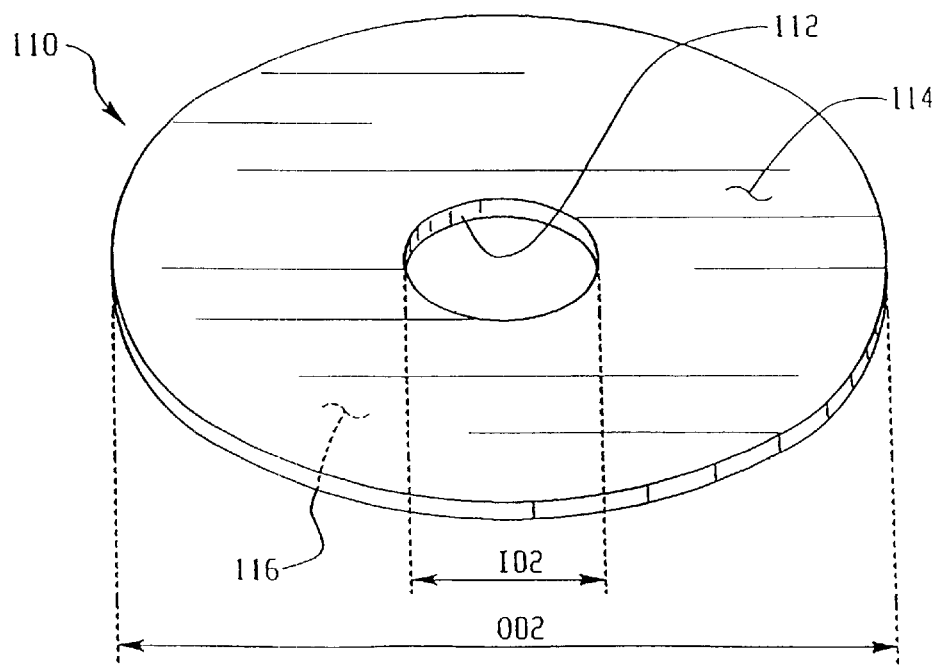
FIG. 4 is a perspective view of a seal member according to a second embodiment of the present invention.

It should be appreciated that while FIGS. 3 and 4 illustrate preferred embodiments of the means for containing sample material within the die cavity, such means may take many other suitable forms. Importantly, the means for containing the sample material acts as a seal at the peripheral edge of the die cavity to inhibit the release of sample material therefrom.

The invention has been described with reference to preferred embodiments. Obviously, modifications and alterations will occur to others upon a reading and understanding of this specification. It is intended that all such modifications and alterations be included insofar as they come within the scope of the appended claims or the equivalents thereof.

Having thus described the invention, it is now claimed:

1. An apparatus for measuring properties of a sample material, comprising:
   (a) a first die assembly including:
      a first die plate having a first diameter,
   (b) a second die assembly including:
      a second die plate rotatable relative to said first die plate and having a second diameter, wherein said first and second die assemblies are movable between an open and closed position, said first and second die plates forming a die cavity for holding a sample material;
   (c) a sealing means located between said first and second die plates to inhibit release of the sample material from the die cavity; and
   (d) wherein neither said first or second die plate contains means for receiving and retaining said sealing means in place relative to said first and second die plates, or less than the first and second diameters.

2. An apparatus according to claim 1, wherein said sealing means has a generally annular shape and an opening defining an inner diameter.

3. An apparatus according to claim 2, wherein said sealing means has a generally circular cross-section.

4. An apparatus according to claim 3, wherein said inner diameter is equal to or less than the first and second diameters.

5. An apparatus according to claim 4, wherein the outer diameter of the sealing means is dimensioned such that a cross-section of said sealing means has a diameter that is greater than or equal to the distance between said first and second die plates at the outer edge thereof, in the closed position.

6. An apparatus according to claim 4, wherein said sample material is located in said opening during testing thereof.

7. An apparatus according to claim 2, wherein said sealing means has a generally triangular cross-section.

8. An apparatus according to claim 1, wherein said sealing means is deformable, said sealing means compressing in response to closure of said first and second die assemblies to seal the peripheral edge of said die cavity.

9. An apparatus according to claim 1, wherein said sealing means has a generally annular disk-like shape and an opening defining an inner diameter.

10. An apparatus according to claim 9, wherein said sealing means has generally planar upper and lower surfaces.

11. An apparatus according to claim 9, wherein said inner diameter is equal to or less than the first and second diameters.

12. An apparatus according to claim 11, wherein said sample material is located in said opening during testing thereof.

13. A method for inhibiting the release of a sample material from a die cavity of a test instrument for measuring properties of the sample material, wherein said die cavity is defined by first and second die plates which are movable between an open and closed position, said method comprising:
   moving the first and second die plates to the open position;
   locating a generally annular seal means between said first and second die plates, wherein neither said first or second die plate contains means for receiving and retaining said seal means in place relative to said first and second die plates;
   locating the sample material within an opening bounded by said seal means;
   moving said first and second die plates to a closed position, wherein said seal means is compressed.

14. The method of claim 13, wherein in response to moving said first and second die plates to a closed position, said seal means is outwardly radially deformable with respect to said first and second die plates to seal said die cavity.

15. The method of claim 13, wherein in response to moving said first and second die plates to a closed position, said seal means is outwardly radially deformable with respect to said first and second die plates to the outer edge of said die cavity to seal said die cavity.

16. The method of claim 13, wherein in response to moving said first and second die plates to a closed position, said seal means is outwardly radially deformable with respect to said first and second die plates to the peripheral edge of said die cavity to seal said die cavity, such that said seal means has minimal contact with said first and second die plates.

17. An apparatus for measuring properties of a sample material, said apparatus comprising:
   (a) a first die assembly including:
      a first die plate having a first diameter,
   (b) a second die assembly including:
      a second die plate rotatable relative to said first die plate and having a second diameter, wherein said first and second die assemblies are movable between an open and closed position, said first and second die plates forming a die cavity for holding a sample material;
   (c) a sealing means located between said first and second die plates to inhibit release of the sample material from the die cavity, wherein neither said first or second die plate contains means for receiving and retaining said sealing means in place, said sealing means being outwardly radially deformable with respect to said first and second die plates in response to closure of said first and second die assemblies.

18. The apparatus of claim 17, wherein in response to closure of said first and second die assemblies said sealing means is outwardly radially deformable with respect to said first and second die plates to the outer edge of said die cavity to seal said die cavity.

19. The apparatus of claim 17, wherein in response to closure of said first and second die assemblies said sealing means is outwardly radially deformable with respect to said first and second die plates to the peripheral edge of said die cavity to seal said die cavity, such that said sealing means has minimal contact with said first and second die plates.

20. The apparatus of claim 17, wherein said sealing means has a generally annular shape.

21. An apparatus according to claim 20, wherein said sealing means has a generally circular cross-section.

* * * * *

UNITED STATES PATENT AND TRADEMARK OFFICE
CERTIFICATE OF CORRECTION

PATENT NO. : 6,336,357 B1
DATED : January 8, 2002
INVENTOR(S) : Pawlowski et al.

It is certified that error appears in the above-identified patent and that said Letters Patent is hereby corrected as shown below:

<u>Column 4,</u>
Line 34, change the word "fluoroclastomer" to -- fluoroelastomer --
Line 36, change the word "scaling" to -- sealing --

<u>Column 5,</u>
Line 11, change the word "scaling" to -- sealing --
Line 12, change the word "rin" to -- run --
Lines 46-47, delete ", or less than the first and second diameters"

Signed and Sealed this

Thirteenth Day of August, 2002

*Attest:*

*Attesting Officer*

JAMES E. ROGAN
*Director of the United States Patent and Trademark Office*